US00PP14998P2

(12) United States Plant Patent
Brown

(10) Patent No.: US PP14,998 P2
(45) Date of Patent: Jul. 6, 2004

(54) PETUNIA PLANT NAMED 'RED MP101'

(50) Latin Name: *Petunia×hybrida*
Varietal Denomination: Red MP101

(75) Inventor: Graham Noel Brown, Pennant Hills (AU)

(73) Assignee: NuFlora International, Pty Ltd., Macquarie Fields (AU)

( * ) Notice: Subject to any disclaimer, the term of this patent is extended or adjusted under 35 U.S.C. 154(b) by 0 days.

(21) Appl. No.: 10/666,279

(22) Filed: Sep. 17, 2003

(51) Int. Cl.[7] ..... A01H 5/00
(52) U.S. Cl. ..... Plt./356
(58) Field of Search ..... Plt./356

*Primary Examiner*—Kent Bell
*Assistant Examiner*—Susan B. McCormick
(74) *Attorney, Agent, or Firm*—C. A. Whealy

(57) ABSTRACT

A new and distinct cultivar of Petunia plant named 'Red MP101', characterized by its compact, outwardly spreading and mounded plant habit; relatively short internodes; dense and bushy growth habit; freely branching habit; small leaf size; and numerous small red-colored flowers.

1 Drawing Sheet

Botanical classification: Petunia×hybrida cultivar Red MP101.

BACKGROUND OF THE INVENTION

The present Invention relates to a new and distinct cultivar of Petunia plant, botanically known as Petunia×hybrida, and hereinafter referred to by the cultivar name Red MP101.

The new Petunia is a product of a planned breeding program conducted by the Inventor in Cobbitty, New South Wales, Australia. The objective of the breeding program is to create outwardly spreading Petunias with numerous small flowers with attractive flower colors.

The new Petunia originated from a cross-pollination made by the Inventor during the spring of 2000 of a proprietary Petunia selection identified as X00.120, not patented, as the female, or seed parent, with a proprietary Petunia selection identified as X00.167, not patented, as the male, or pollen parent. The new Petunia was selected as a single plant from the resulting progeny of the cross-pollination by the Inventor in 2000, in Cobbitty, New South Wales, Australia, on the basis of its outwardly spreading habit and numerous small red-colored flowers.

Asexual reproduction of the new cultivar by vegetative cuttings taken in Cobbitty, New South Wales, Australia since 2000 has shown that the unique features of this new Petunia are stable and reproduced true to type in successive generations.

SUMMARY OF THE INVENTION

Plants of the cultivar Red MP101 have not been observed under all possible environmental conditions. The phenotype may vary somewhat with variations in environment such as temperature and light intensity without, however, any variance in genotype.

The following traits have been repeatedly observed and are determined to be the unique characteristics of 'Red MP101'. These characteristics in combination distinguish 'Red MP101' as a new and distinct cultivar:

1. Compact, outwardly spreading and mounded plant habit.

2. Relatively short internodes, dense and bushy growth habit.
3. Freely branching habit.
4. Small leaf size.
5. Numerous small red-colored flowers.

Plants of the new Petunia and the female parent differ in flower color as plants of the female parent have dark pink-colored flowers. Compared to plants of the male parent, plants of the new Petunia have smaller leaves and smaller flowers.

Plants of the new Petunia can be compared to plants of the cultivar Dancasred, not patented. In side-by-side comparisons conducted in Cobbitty, New South Wales, Australia, plants of the new Petunia differed from plants of the cultivar Dancasred in the following characteristics:

1. Plants of the new Petunia had shorter internodes than plants of the cultivar Dancasred.
2. Flowers of plants of the new Petunia had smaller leaves than plants of the cultivar Dancasred.
3. Plants of the new Petunia had smaller flowers than plants of the cultivar Dancasred.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Petunia.

The photograph at the top of the sheet comprises a side perspective view of a typical flowering plant of 'Red MP101' grown in a container.

The photograph at the bottom of the sheet comprises a close-up view of typical leaves and flowers of 'Red MP101'.

DETAILED BOTANICAL DESCRIPTION

The aforementioned photographs and following observations and measurements describe plants grown in Lompoc, Calif., under commercial practice during the winter and spring in a polycarbonate-covered greenhouse with day temperatures about 18 to 24° C., night temperatures about 16 to 18° C. and light levels about 4,000 to 8,000 foot-candles. Plants were grown with one rooted cutting per 10-cm container for about 11 weeks. In the following description, color references are made to The Royal Horticultural Society Colour Chart, 1995 Edition, except where general terms of ordinary dictionary significance are used.

Botanical classification: Petunia×hybrida cultivar Red MP101.

Parentage:

*Female parent*.—Proprietary Petunia selection identified as X00.120, not patented.

*Male parent*.—Proprietary Petunia selection identified as X00.167, not patented.

Propagation:

*Type cutting*.—Vegetative cuttings.

*Time to initiate roots*.—About 14 days at 22° C.

*Time to develop roots*.—About 28 days at 22° C.

*Root description*.—Fine, fibrous, whitish in color.

*Rooting habit*.—Freely branching, dense.

Plant description:

*Form*.—Annual flowering plant; indeterminate; compact; initially upright, then outwardly spreading and mounded; plants eventually becoming hemispherical in shape. Vigorous growth habit. Freely basal branching with about eight main lateral branches per plant with lateral branches potentially forming at every node.

*Usage*.—Appropriate for hanging baskets, window boxes, patio containers and landscape applications.

*Plant height*.—About 12 cm.

*Plant diameter*.—About 32 cm.

*Lateral branches*.—Length: About 14 cm. Diameter: About 2 mm. Internode length, vegetative shoots: About 1 cm. Internode length, flowering shoots: About 1.5 to 2 cm. Texture: Pubescent. Color: 144C.

*Foliage description*.—Arrangement, before flowering: Alternate, simple. Arrangement, when flowering: Opposite, simple. Length: About 3 cm. Width: About 1.5 cm. Shape: Elliptical. Apex: Broadly acute. Base: Attenuate. Margin: Entire. Texture: Glandular, viscid; pubescent. Venation pattern: Pinnate. Color: Developing and fully expanded foliage, upper surface: 146A. Developing and fully expanded foliage, lower surface: 146B. Venation, upper surface: 146C. Venation, lower surface: 146D. Petiole length: About 4 mm. Petiole diameter: About 2 mm. Petiole color: 144C.

Flower description:

*Flower type and habit*.—Small salverform flowers; flowers face mostly upward or outward; single, axillary. Flowers persistent. Freely flowering, typically more than 200 open flowers and flower buds per plant.

*Natural flowering season*.—Long day responsive; spring until frost in the autumn; flowering continuous during the flowering period.

*Flower longevity on the plant*.—About seven to ten days.

*Fragrance*.—None detected.

*Flower size*.—Diameter: About 3 cm. Tube length: About 3 cm. Throat diameter, distal end: About 8 mm. Tube diameter, proximal end: About 2.5 mm.

*Flower buds*.—Length: About 2 cm. Diameter: About 4 mm. Shape: Elongated oblong with ruffled apices. Color: 195B.

*Corolla*.—Arrangement/appearance: Single whorl of five petals, fused into flared trumpet with distinct clefts between petal lobes. Petal length from throat: About 1.3 to 1.5 cm. Petal width: About 1.7 cm. Petal shape: Roughly fan-shaped or obovate. Petal apex: Slightly emarginate. Petal margin: Entire; slightly sinuate. Petal texture, upper and lower surfaces: Smooth, velvety. Color: Petal, upper surface, when opening: 46A. Petal, lower surface, when opening: More gray than 186C. Petal, upper surface, fully opened: Slightly darker or more crimson than 45A; color becoming closer to 50A with 185D towards the margins with development. Petal, lower surface, fully opened: More gray than 50D. Flower throat (inside): 196C to 196D. Flower tube (outside): 196A. Venation, upper petal surface: 46A. Venation, lower petal surface: 50D. Venation, throat: 187B. Venation, tube: 146D.

*Sepals*.—Arrangement/appearance: Single whorl of five sepals fused at base, star-shaped. Length: About 1 cm. Width: About 2 mm. Shape: Ligulate. Apex: Broadly acute to rounded. Margin: Entire. Texture, both surfaces: Glandular; pubescent. Color, upper and lower surfaces: 146A.

*Peduncles*.—Length: About 3.7 cm. Width: About 1.25 mm. Angle: About 45° to the stem. Strength: Strong; wiry. Texture: Pubescent. Color: 144B.

*Reproductive organs*.—Stamens: Quantity/arrangement: Five, adnate to corolla tube. Anther shape: Ovoid. Anther length: Less than 1 mm. Anther color: 158A. Pollen amount: Scarce. Pollen color: 158C. Pistils: Quantity: One. Pistil length: About 1.1 cm. Stigma shape: Anvil-shaped. Stigma color: 144B. Style length: About 8 mm. Style color: 144D. Ovary color: 144A.

*Fruit/seed*.—Fruit and seed production has not been observed.

Disease/pest resistance: Plants of the new Petunia have not been observed to be resistant to pathogens and pests common to Petunia.

It is claimed:

1. A new and distinct cultivar of Petunia plant named 'Red MP101', as illustrated and described.

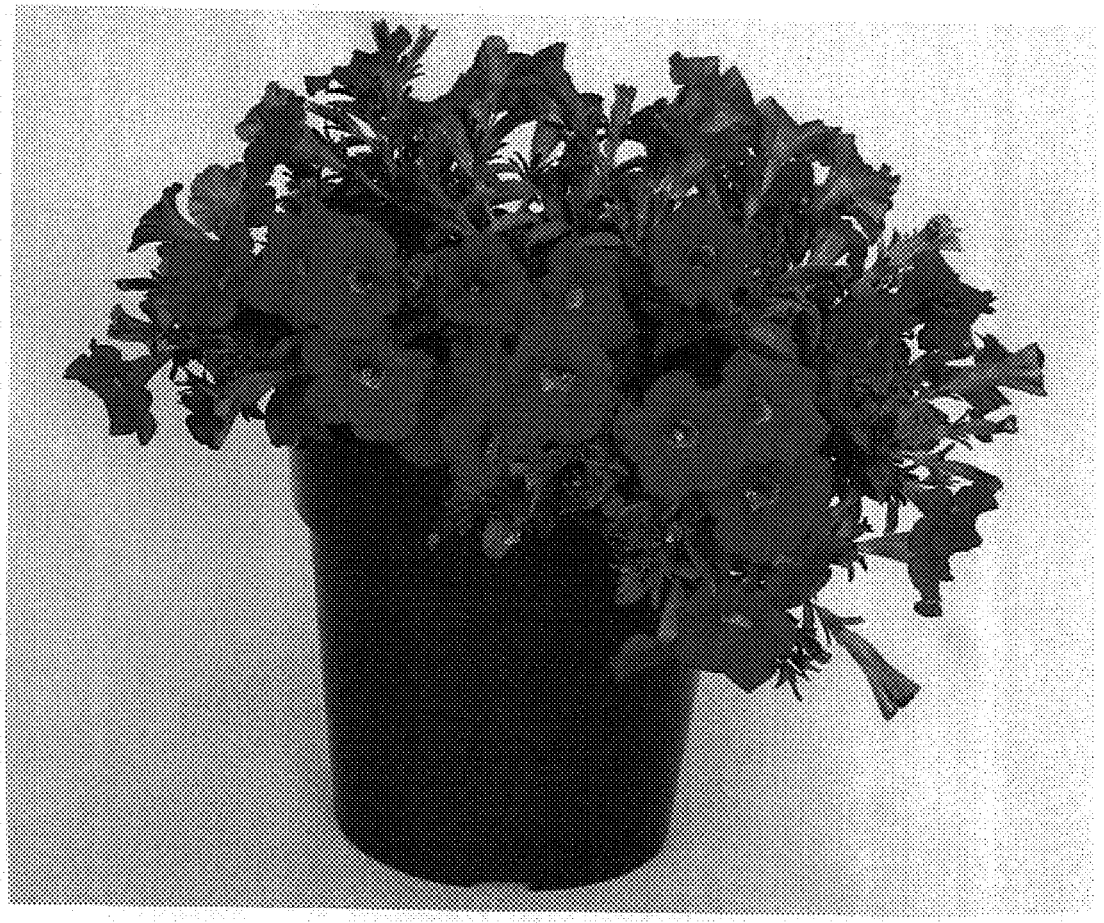
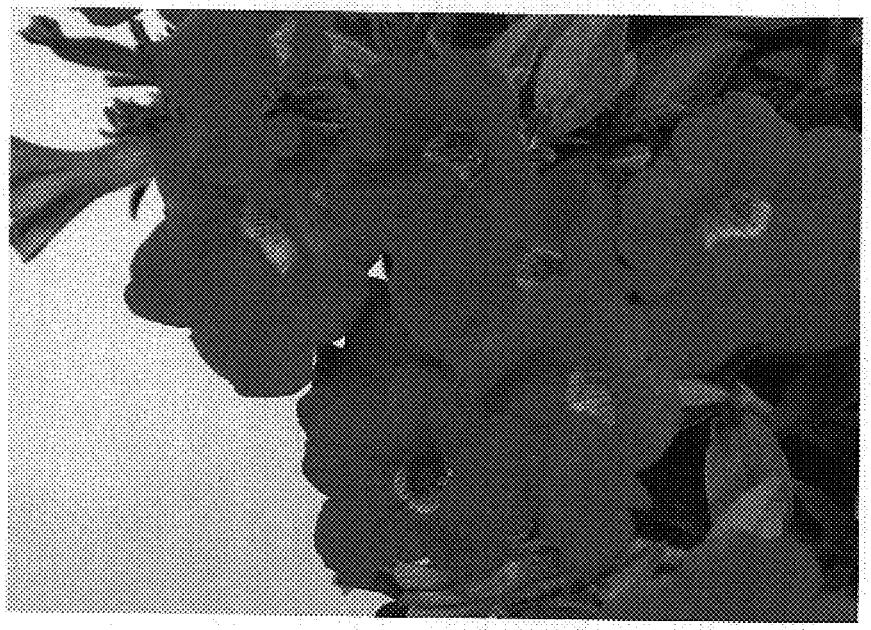

* * * * *